United States Patent [19]
Helfrich et al.

[11] 4,392,864
[45] Jul. 12, 1983

[54] STABILIZED ROMANOWSKY STAIN SOLUTION

[75] Inventors: Elaine A. Helfrich; Kin F. Yip, both of Elkhart, Ind.

[73] Assignee: Miles Laboratories, Inc., Elkhart, Ind.

[21] Appl. No.: 344,390

[22] Filed: Feb. 1, 1982

[51] Int. Cl.³ .................. C09B 44/00; G01N 1/00
[52] U.S. Cl. .................................... 8/506; 8/638; 8/644; 8/654; 424/3; 424/11
[58] Field of Search .............. 8/506, 638, 644, 654; 424/3, 11

[56] References Cited

U.S. PATENT DOCUMENTS 4,290,769  9/1981  Liad et al. ..................... 8/506
4,363,632  12/1982  Custard et al. ............... 8/506

OTHER PUBLICATIONS

Lillie, R. D., *J. Lab. Clin. Med.*, 1944, 29, 1181–1197.
Marshall, P. N., *Histochemical J.*, 1978, 10, 1–29.
E. Qurr and N. Anand, in Venkataraman's "The Chemistry of Synthetic Dyes," vol. VII, Academic Press, 1974, pp. 279 and 288.
Gilliland et al., *Stain Technology* (1979), vol. 54, No. 3, pp. 141–150.
Marshall et al., *J. Clin. Pathol.*, 28:920–923, (1975).

*Primary Examiner*—A. Lionel Clingman
*Attorney, Agent, or Firm*—Jerome L. Jeffers

[57] ABSTRACT

Disclosed is a Romanowsky stain having improved stability characteristics which comprises a methanol solution of Methylene Blue, an azure dye and the free acid of Eosin Y.

4 Claims, No Drawings

STABILIZED ROMANOWSKY STAIN SOLUTION

BACKGROUND OF THE INVENTION

This invention relates to blood staining systems and, more particularly, to the stabilization of Romanowsky-type stains, e.g., Wright's solution and Giemsa's solution. These stains comprise a methanol solution of a Methylene Blue and an eosin dye along with other allied dyes. Typical allied dyes include Azure A, Azure B and Azure C with Eosin Y being the preferred eosin dye which is typically introduced to the methanol solution in the form of its disodium salt.

In order to employ such a stain, it is usually necessary to prepare a solution of the dry stain in methyl alcohol and apply the solution to a blood smear or the like. Next, a buffer solution and a rinse solution are added stepwise to the stained smear until a differential stain of cells occurs on the smear when observed with the microscope.

The presence of a second dye, in addition to Methylene Blue, particularly Eosin Y, is desirable to enhance the staining qualities of the solution. Other allied dyes, i.e., Azure A, Azure B and Azure C are also desirable for their enhancement of the solution's ability to stain the blood smear. The standard way of using such dyes is to form the methanol solution and allow it to stand for a period of time. The azure dyes in the stain powder are not very soluble in methanol, and Methylene Blue degrades into azures by a demethylation reaction in the presence of eosin upon aging in solution. It will normally take about two weeks of standing for the optimal staining result to be achieved. Unfortunately, the dyes continue to degrade, and the resultant degradation products render the solution unsuitable for the intended purpose. Furthermore, random precipitation in the stain solution upon aging results in poor stain quality. Thus, while the stain solution takes about two weeks to become fully effective, it has a shelf life of only about 3 to approximately 12 months.

Gilliland et al report in *Stain Technology*, Vol. 54, No. 3, pp. 141-150 that a Romanowsky-type blood stain can be stabilized by making the solution acidic to protonate the eosin thereby inhibiting the formation of the precipitate. For use, the stain is neutralized by a specially formulated fixative solution. We have found that this technique is not suitable for the stabilization of dyes of the concentration necessary for suitability in certain automated staining devices. This concentration should be at least sufficient to provide a solution which, when scanned by spectrophotometer, will absorb 230 optical density units at 645 nanometers (nm) and 128 optical density units at 525 nm because of the required short staining time in such automated devices. As used herein, an optical density unit is defined as the absorbance multiple of the dilution factor, i.e., it is a function of concentration. For example, a solution which exhibited an absorbance by spectrophotometric measurement of 0.575 at a wavelength of 645 nm after it had been diluted 400 times would absorb 0.575×400 or 230 optical density units. Absorption measurements are made at these wavelengths because a solution of Methylene Blue and azures gives an absorption maximum at 645 nm and, a solution of Eosin Y gives an absorption maximum at 525 nm. While Gilliland et al do not disclose the concentration of their stain solution in the cited article, judging from the absorbance data they disclose in their FIG. 1, the concentration of their stain is estimated to be at a level of optical density of about 162 optical density units at 645 nm and 87.5 optical density units at 525 nm which is about 70% of the concentration required for suitability of the solution in automated staining devices referred to above. In acidifying stain solutions of the required concentration by the addition of HCl, it has been found that acidification to pH 3.0 as disclosed by Gilliland et al is insufficient to prevent precipitation in the more concentrated staining solutions which are useful in the automatic staining devices. Further acidification to pH 1.6 will prevent precipitation but at this pH, the Eosin Y is irreversibly converted to some other species which degrades the staining performance of the dye.

Marshall et al disclose in *J. Clin. Pathol.*, 28: 920923 (1975) the preparation of a Romanowsky-type stain by dissolving Methylene Blue, Azure B and the free acid of an eosin dye in a 1:1 v/v mixture of glycerol and methanol. They describe this solution as being extremely stable although they report that conventional Romanowsky-type stains show similar stability. In any event, a stain solution in which the solvent is 50% glycerol is known to be highly stable but has such a high viscosity that it is unsuitable for use in automated staining devices.

SUMMARY OF THE INVENTION

The present invention is a method for preparing a Romanowsky stain solution having improved stability characteristics which comprises dissolving in methanol a mixture of Methylene Blue, Azure A, Azure B or Azure C and the free acid of Eosin Y in such amounts that the resulting solution exhibits spectrophotometric absorption of at least about 230 optical density units at 645 nm and 128 optical density units at 525 nm.

DESCRIPTION OF THE INVENTION

It has now been discovered that a Romanowsky-type stain having improved stability characteristics can be prepared in methanol and in the concentration needed for use in automated staining devices by employing the free acid of Eosin Y rather than its disodium salt.

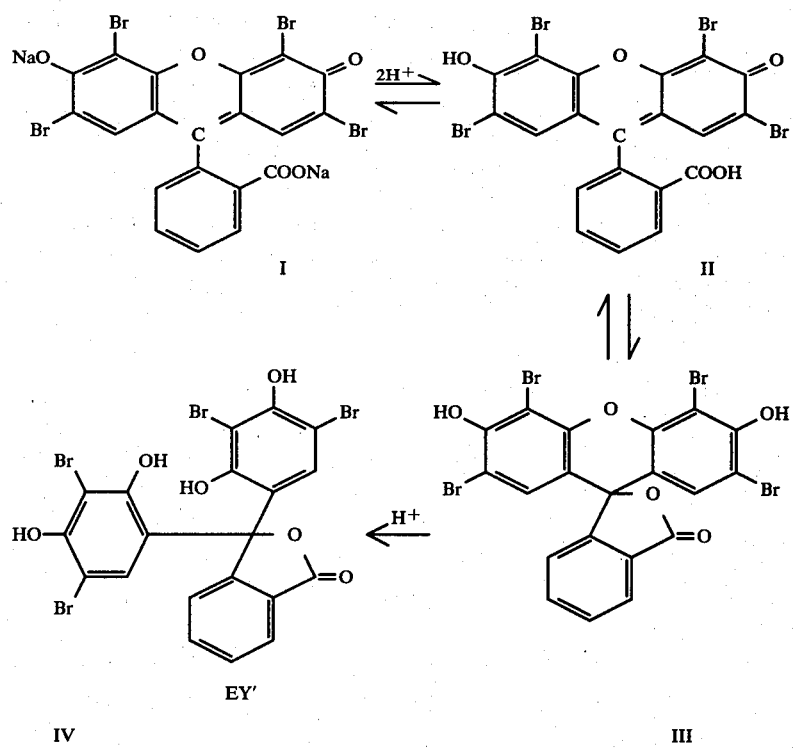

SCHEME A

The chemistry involved in this invention is illustrated by the structural formulae of scheme A. While Eosin Y is normally marketed in the form of its disodium salt (I), it can readily be converted to its free acid (II) as indicated by the foregoing equation. The carboxyl group of the free acid exists in equilibrium with its lactone (III) which upon further acidification is irreversibly converted to a species (IV) which for convenience is referred to as EY'. Compound II can be generated by acidifying a stain solution containing at least about 0.53 g/ml Eosin Y (disodium salt) which is necessary for effective performance in automated staining devices and is equivalent in staining performance to compound I. However, this material was observed to precipitate from methanol solution at these concentrations. Further acidification, to pH 1.6 prevents precipitation but causes the formation of compound IV (EY') which is deficient in staining performance. Since direct acidification of the methanolic stain solution unavoidably generates precipitation or overacidification at the Eosin Y concentrations under consideration, the usefulness of the free acid of Eosin Y was investigated. Thus, rather than convert compound I to its free acid II in situ by acidifying the methanolic solution, the free acid is used directly in preparing the solution to provide a modified Wright stain comprising Methylene Blue, the free acid of Eosin Y and Azure A, Azure B or Azure C. The pH (MeOH) of the preparations were found to be between 2.5 and 3.0, the thiazines were found to be very stable and no changes in Methylene Blue and azures were detected at room temperature for 30 days with about 0.2% of EY' formation being determined by high performance liquid chromatograph (HPLC). About two percent of the Eosin Y was found to have degraded to EY' after aging at 60° C. for 30 days. No precipitation was detected in stain samples kept at 60° C., room temperature and 5° C. as determined by absorption spectroscopy, HPLC analysis or microscopic examination.

A typical formulation prepared by the method of this invention involves the dissolution of about 0.64 to 1.0 grams per liter (g/l) Methylene Blue, 0.49 to 1.0 g/l of the free acid of Eosin Y and 0.32 to 1 g/l of an allied dye, i.e., Azure A, Azure B or Azure C. The presence of Eosin Y in addition to Methylene Blue is necessary to enhance the staining qualities of the solution.

The method of practicing the invention and the advantages inherent therein are further illustrated by the following examples:

EXAMPLE I

A methanolic solution was prepared by dissolving commercial Wright stain powder (a mixture of Methylene Blue, the disodium salt of Eosin Y and an allied azure dye) in a concentration of 3 gm in about 1,000 ml of methanol. The solution had absorbance of 0.575 at 645 nm and 0.320 at 525 nm after it was diluted 400 times with methanol. Hence, the solution had the required 230 optical density units at 645 nm and 128 optical density units at 525 nm. The solution was acidified with methanolic hydrogen chloride (0.96 N) to pH (MeOH) 3.1. This, according to the previously mentioned article by Gilliland et al, is sufficiently acidic to convert the disodium salt of Eosin Y to its free acid. However, instead of providing a stable solution, this method provided a solution in which substantial precipitation was observed when it was stored at room temperature, 5° C. and 60° C. for 3 hours, 3 days and 60 days, respectively.

EXAMPLE II

A methanolic solution was prepared with commercial Wright stain powder as in Example I and was acidified with methanolic hydrogen chloride (0.96 N) to pH (MeOH) 1.6. After aging for three days at 60° C. about 10% of the Eosin Y was found to have degraded to EY' which resulted in a deterioration of stain performance and rendered it unsuitable for its intended purpose because of the effective Eosin Y concentration being diminished.

EXAMPLE III

A methanolic solution was prepared by dissolving Methylene Blue (concentration equivalent to 0.71 g/l), Eosin Y free acid (concentration equivalent to 0.55 g/l) and Azure C (concentration equivalent to 0.36 g/l) in methanol. This solution absorbed 230 optical density units at 645 nm and 128 optical density units at 525 nm. The absorption was measured after the solution was diluted 400 times with methanol. After stressing the solution at 60° C. for 30 days, the spectrophotometric absorption had not changed. There was no observable precipitation and no deterioration of Methylene Blue was detected by HPLC. This is in contrast to a solution prepared as described in Example I, in which the Eosin Y was in the form of its disodium salt, wherein the absorption of Methylene Blue and the azure dye had degenerated by more than half to 103.5 optical density units at 645 nm.

EXAMPLE IV

The stain solution prepared as described in Example III was tested in the HEMATEK I ® and HEMATEK II ® automated tissue staining devices. This stain was found to be equivalent to a solution of commercial Wright stain exhibiting absorption of 230 and 128 optical density units at 645 nm and 525 nm, respectively.

What is claimed is:

1. A method for the preparation of a Romanowsky-type stain solution having improved stability characteristics which comprises dissolving in methanol a mixture of Methylene Blue, Azure A, Azure B, Azure C or a combination of these azure dyes and the free acid of Eosin Y in such amounts that the resulting solution exhibits spectrophotometric absorption of at least 230 optical density units at 645 nm and 128 optical density units at 525 nm.

2. The method of claim 1 wherein the stain is prepared by dissolving the equivalent of 0.64 to 1.0 g/l Methylene Blue, 0.49 to 1.0 g/l of the free acid of Eosin Y and 0.32 to 1.0 g/l of the azure dye in methanol.

3. A Romanowsky-type stain solution having improved stability characteristics which comprises a methanolic solution of Methylene Blue; Azure A, Azure B, Azure C or a combination of these azure dyes and the free acid of Eosin Y with the Methylene Blue and azure dye being present in a concentration which results in spectrophotometric absorption of at least 230 optical density units at 645 nm and the free acid of Eosin Y is present in an amount which results in spectrophotometric absorption of at least 128 optical density units at 525 nm.

4. The stain of claim 3 wherein the methanol solution contains the equivalent of 0.64 to 1.0 g/l Methylene Blue, 0.49 to 1.0 g/l of the free acid of Eosin Y and 0.32 to 1.0 g/l of the azure dye.

* * * * *